United States Patent
Brun et al.

(10) Patent No.: US 9,377,668 B2
(45) Date of Patent: Jun. 28, 2016

(54) DEVICE FOR NON-LINEAR SIGNAL CONVERSION BY FOUR-WAVE MIXING

(71) Applicant: COMMISSARIAT A L'ENERGIE ATOMIQUE ET AUX ENE ALT, Paris (FR)

(72) Inventors: Mickael Brun, Eybens (FR); Pierre Labeye, Grenoble (FR); Sergio Nicoletti, Sinard (FR); Adonis Bogris, Athenes (GR); Alexandros Kapsalis, Athenes (GR); Dimitris Syvridis, Athenes (GR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 219 days.

(21) Appl. No.: 14/307,842

(22) Filed: Jun. 18, 2014

(65) Prior Publication Data

US 2014/0376854 A1 Dec. 25, 2014

(30) Foreign Application Priority Data

Jun. 25, 2013 (EP) .................................... 13305876

(51) Int. Cl.
*G02B 6/10* (2006.01)
*G02F 1/35* (2006.01)
(Continued)

(52) U.S. Cl.
CPC .............. *G02F 1/3536* (2013.01); *G02B 6/102* (2013.01); *G01N 21/3504* (2013.01); *G01N 21/7703* (2013.01); *G02B 2006/12176* (2013.01); *G02F 2202/105* (2013.01)

(58) Field of Classification Search
CPC ............................. G02F 1/3536; G02B 6/102
See application file for complete search history.

(56) References Cited

U.S. PATENT DOCUMENTS

2007/0012940 A1* 1/2007 Suh ........................ H01L 33/507 257/99
2013/0034113 A1* 2/2013 Oba ...................... H01S 3/0675 372/6

(Continued)

FOREIGN PATENT DOCUMENTS

EP 2 042 918 A1 4/2009

OTHER PUBLICATIONS

Y. Huang, et al., "eSNR Improvement in Indirect Detection of mid-IR Signals by Wavelength Conversion in SOS Waveguides", Proc SPIE 8155 Infrared Sensors, Devices, and Applications; and Single Photon Imaging II, vol. 8155, (2011), pp. 81550U1 to 81550U-7.

(Continued)

*Primary Examiner* — Jerry Rahll
(74) *Attorney, Agent, or Firm* — Oblon, McClelland, Maier & Neustadt, L.L.P.

(57) ABSTRACT

A device for non-linear conversion of first infrared signal into a second infrared signal with a wavelength that is less than that of the first infrared signal by means of four-wave mixing, which includes at least one portion of SiGe arranged on at least one first layer of material with a refractive index which is less than that of silicon, a germanium concentration in the portion of SiGe which varies continuously between a first value and a second value which is greater than the first value, in a direction which is approximately perpendicular to a face of the first layer on which the portion of SiGe is arranged, and in which a summital part of the portion of SiGe where the germanium concentration is equal to the second value is in contact with a gas and/or a material with a refractive index which is less than that of the silicon.

17 Claims, 7 Drawing Sheets

(51) Int. Cl.
*G01N 21/3504* (2014.01)
*G02B 6/12* (2006.01)
*G01N 21/77* (2006.01)

(56) References Cited

U.S. PATENT DOCUMENTS

2014/0007921 A1* 1/2014 Kuramachi ............ B82Y 20/00
　　　　　　　　　　　　　　　　　　　　　　　136/247
2016/0027971 A1* 1/2016 Anc ..................... C09K 11/025
　　　　　　　　　　　　　　　　　　　　　　　257/98

OTHER PUBLICATIONS

En-Kuang Tien, et al., "Discrete parametric band conversion in silicon for mid-infrared applications", Optics Express, vol. 18, No. 21, (Oct. 11, 2010), pp. 21981-21989.

Govind P. Agrawal, "Nonlinear Fiber Optics", Optics an Photonics, 3$^{rd}$ Edition, Academic Press, (2001), 467 pages.

Goran Z. Mashanovich, et al., "Low loss silicon waveguides for the mid-infrared", Optics Express, vol. 19, No. 8, (Apr. 11, 2011), pp. 7112-7119.

Fangxin Li, et al., "Low propagation loss silicon-on-sapphire waveguides for the mid-infrared", Optics Express, vol. 19, No. 16, (Aug. 1, 2011), pp. 15212-15220.

Richard Soref, "Mid-infrared photonics in silicon and germanium", Nature Photonics, vol. 4, (Aug. 2010), pp. 495-497.

Sanja Zlatanovic, et al., "Mid-infrared wavelength conversion in silicon waveguides using ultracompact telecom-band-derived pump source", Nature Photonics, vol. 4, (Aug. 2010), pp. 561-564.

European Search Report Issued Nov. 6, 2013 in EP application 13305876, filed on Jun. 25, 2013 ( with English Translation of Categories of Cited Documents).

M.A. Ettabib et al "FWM-based Wavelength Conversion in a silicon Germanium Waveguide", OFC/NFOEC Technical Digest, 2013, 3 pages.

Pierre Barritault et al. "Mlines characterization of the refractive index profile of SiGe gradient waveguides at 2.15 μm", Optics Express, vol. 21, No. 9, 2013, 10 pages.

K. Hammani et al. "Linear and Nonlinear Properties of SiGe Waveguides at Telecommunication Wavelengths", OFC/NFOEC Technical Digest, 2013, 3 pages.

Nick K. Hon et al. "the third-order nonlinear optical coefficients of Si, Ge, and $Si_1$—$Ge_x$ in the midwave and longwave infrared", Journal of Applied Physics 110, 011301, 2011, 8 pages.

* cited by examiner

DEVICE FOR NON-LINEAR SIGNAL CONVERSION BY FOUR-WAVE MIXING

TECHNICAL FIELD

The invention relates to the domain of guided optics, in particular in the mid infrared wavelength range (also called "MidIR"), that is, the domain of wavelengths between about 3 μm and 7.5 μm.

The invention relates in particular to a device for the non-linear conversion of a first infrared signal into a second infrared signal whose wavelength is less than that of the first infrared signal, by means of four-wave mixing, and in particular by means of degenerate four-wave mixing. The invention also relates to a process for making such a device. The device according to the invention may be used to form a non-linear waveguide which allows a first infrared signal with a wavelength which belongs to the MidIR domain to be converted into a second infrared signal with a wavelength which belongs to the near infrared domain (also called "NIR") and which corresponds to wavelengths between 1.3 μm and 1.9 μm, used, for example, in integrated IR optics or free-space communication applications.

The invention also relates to the domain of gas sensors, and in particular a gas sensor of the NDIR ("Non Dispersive InfraRed") type used for example in the domains of security (detection of illicit substances, explosives, of people, etc.), testing of industrial gas emissions for environmental protection purposes, detection of gas in dwellings, the automotive field, and health.

PRIOR ART

The family of gas optical sensors is differentiated from other types of gas sensors by their high selectivity for the gas to be detected. They are based on the use of an infrared source which emits in the MidIR wavelength range, and which excites vibrational transitions in the gas to be detected. The concentration of the gas being detected can be measured by various means which may be, for example, of the NDIR, photo-acoustic or even the ICLAS type. An NDIR-type sensor directly measures the absorption due to the gas at the excitation wavelength of the gas after the light has passed through the gas. The use of QCL ("Quantum Cascade Laser") type infrared sources allows miniaturisation of this type of sensor to be achieved. Miniaturisation can also be achieved through the development of integrated optical elements suitable for transporting and for processing the MidIR signal with low losses and of effective system for detection in the MidIR allowing effective measurement of attenuation of the light beam by the gas.

In the MidIR wavelength range, the detectors that are available on the market have a detection efficiency which is typically several orders of magnitude less than the detectors developed for the near infrared, in particular for telecoms applications and which generally function around a wavelength which is equal to about 1.55 μm. The best NIR-type detectors are often cooled to a low temperature either using a multi-stage Peltier system or by cryogenic fluid in order to compensate for high leakage currents which are a hindrance to the development of a miniature integrated gas sensor. In order to resolve this problem the document by Huang et al., Proc SPIE 8155 Infrared Sensors, Devices, and Applications; and Single Photon Imaging II, 81550U (2011) proposes integrating a non-linear element to enable conversion of MidIR wavelength to NIR wavelengths for which effective ambient temperature detectors are available and which may be readily integrated. Such a solution also increases the detection signal-to-noise ratio relative to detection carried out directly in the MidIR range. In order for this solution to be viable a non-linear conversion element which is as efficient as possible, which consumes the lowest possible amounts of energy and which is compatible with QCL lasers, that is, which operates in TM (magnetic transmission) mode, is required.

The wavelength conversion is achieved in a dedicated integrated optical element and uses a third-order non-linear phenomenon which is produced in the material of which it is formed. This element is an optical waveguide with a specifically adapted design. When three different wavelengths are introduced into this conversion element it generates a fourth wavelength due to an effect known as four-wave mixing. In the degenerate version of this phenomenon which occurs in the conversion element, it is sufficient to introduce only two incident wavelengths which correspond, respectively, to a signal to be converted and a signal known as the pump signal. In this case two incident photons from the pump signal interact with one photon from the signal to be converted and give rise to a third photon. These third photons form an output signal called the "idler" signal whose wavelength differs from those of the signal to be converted and the pump signal. The law of conservation of energy means that the frequencies of the waves that are involved satisfy the following fundamental relationship, and therefore sets the accessible wavelengths:

$$2f_p = f_s + f_i \quad (1)$$

where fp, fs and fi correspond to the frequencies of the pump signal, the signal for conversion and idler signal respectively.

In addition the power conversion efficiency of the pump signal to the idler signal depends to a large extent on the chromatic dispersion in the waveguide. Phase matching between the various waves at the pump signal wavelength, expressed as zero chromatic dispersion, is required, and is expressed in the following relationship:

$$2k_p = k_s + k_i \quad (2)$$

where kp, ks and ki correspond to propagation constants of the pump signal, the signal for conversion and idler signal respectively.

The conversion efficiency also depends on the factor γ.Pp.Leff in quadratic manner, where γ is a coefficient which is proportional to the Kerr coefficient for the material used in the conversion element, and which is inversely proportional to the size of the propagated optical mode. Pp is the power of the pump signal and Leff is the effective non-linear length, which depends on the attenuation in the conversion element material in accordance with the relationship Leff=$(1-e^{-\alpha L})/\alpha$, where α corresponds to the attenuation coefficient for the constituent material of the conversion element and therefore to the optical propagation losses in the optical guide, and where L corresponds to the length of the guide. For a guide whose core is large compared to the wavelength, several discrete propagation modes are allowed (so-called multimode guides) whereas for guides whose size is in the region of the wavelength or smaller only a single mode is allowed (so-called monomode).

Various platforms exist for creating integrated waveguides which operate in the MidIR domain, and therefore for creating a non-linear conversion element as described above. The most widely-known waveguides are silicon/silica waveguides which are widely used for telecom applications but whose bandwidth is limited within the MidIR domain on the one hand by the presence of silica, which strongly absorbs wavelengths greater than about 3.6 μm and on the other hand due to the silicon, which absorbs beyond about 7.5 μm. The best levels of performance reported in MidIR are for waveguides made of silicon on a SOI substrate, which exhibit losses of between 0.6 and 0.7 dB/cm at a wavelength of about 3.39 μm. More recently several types of waveguides have been proposed:

silicon on sapphire waveguides which exhibit losses of less than about 2 dB/cm at a wavelength of about 5.18 μm;
germanium waveguides;
SiGe waveguides which exhibit optical index gradients.

The document by E-K Tien et al., "Discrete parametric band conversion in silicon for mid-infrared applications", Optics Express 18, vol. 18, no. 21, pages 21981-21989 (2010) describes a waveguide 10 of the silicon-on-sapphire type (also known as SOS waveguides) in "Slab" or strip form, shown schematically in FIG. 1.

This waveguide 10 includes a sapphire-based substrate 12 on which a layer of silicon 14 of thickness e is made. The silicon layer 14 includes a portion 16 with a width equal to w and a thickness h which is greater than the thickness e of the rest of the layer 14. The silicon portion 16 is surrounded by air or by sapphire 18. The engineering of the form of the waveguide 10, in particular the choice of the value of h, allows the wavelength for which there is zero chromatic dispersion to be determined (that is, which satisfies relationship (2) above), and from a general point of view allows the chromatic dispersion of the waveguide 10 around this wavelength to be limited. Chromatic dispersion plots (in ps/nm/km) as a function of the wavelength λ (in μm) for the waveguide 10 are shown in FIG. 2 for various values of the thickness e of the silicon layer 14 (plot 22: e=100 nm; plot 24: e=200 nm; plot 26: e=300 nm; plot 28: e=400 nm; plot 30: e=500 nm), for a height h=1 μm and width w=1 μm.

For such a waveguide 10, it can therefore be seen that the chromatic dispersion remains relatively high. Moreover, the chromatic dispersion plots represented in FIG. 2 illustrate the fact that in such a waveguide 10 the chromatic dispersion varies greatly in the MidIR range, for example between around 250 ps/nm/km and 1000 ps/nm/km for wavelengths between about 4 μm and 6 μm. This variation increases the tunability requirements for the pump signal source whose role is to preserve phase matching and therefore should be properly tuned in the wavelength in order to compensate for the dispersion variations in the MidIR domain.

In addition, for a waveguide 10 having a length of about 1 cm, the conversion performance levels described in this document were calculated using two approximations in particular: the first is that propagation losses in the waveguide 10 are not taken into consideration, and the second is that a 100% overlap of modes between the wavelengths of the pump signal and the MidIR type signal is assumed, which is in reality untrue. These two approximations tend to result in a final overestimate of the conversion efficiencies stated for such a waveguide 10.

With such a waveguide 10 the chromatic dispersion that is obtained allows a MidIR signal to be converted from a first wavelength band of between 4.2 μm and 5.2 μm into a second wavelength band between 1.48 μm and 1.52 μm. The pump signal wavelength is consequently tuned in order to satisfy the law of conservation of energy (relationship (1) earlier) and the phase matching condition (relationship (2) earlier), and is therefore between 2.18 μm and 2.38 μm. With these parameters a conversion efficiency of −3 dB for a pump power density of 1 GW/cm² may be achieved; that is, an equivalent of 10 W introduced into the waveguide. Such a pump power value does not allow such an object to be integrated on an electronic chip in order for it to be used as a gas detector. More efficient non-linear elements must therefore be sought.

PRESENTATION OF THE INVENTION

Thus there is a need to propose a device for the non-linear conversion of a first infrared signal into a second infrared signal whose wavelength is less than that of the first infrared signal which, in the wavelength range of the second infrared signal, allows a lower and more constant chromatic dispersion to be obtained, especially in the MidIR domain, than that obtained with devices in the prior art, thus allowing more efficient wavelength conversion to be achieved over a wider range of wavelengths.

In order to achieve this, one embodiment proposes a device for a non-linear conversion of a first infrared signal into a second infrared signal whose wavelength is less than that of the first infrared signal by four wave mixing, comprising at least one portion of SiGe arranged on at least one first layer of material whose refractive index, or optical index, is less than that of silicon, wherein a germanium concentration in the portion of SiGe varies continuously between a first value and a second value which is greater than the first value along a direction which is approximately perpendicular to a face of the first layer on which the portion of SiGe is arranged, and in which a summital part of the portion of SiGe in which the germanium concentration is equal to the second value is in contact with a gas and/or a material whose refractive index is less than that of silicon.

It is also discloses a device suitable for a non-linear conversion of a first infrared signal into a second infrared signal whose wavelength is less than that of the first infrared signal by four-wave mixing, comprising at least one portion of SiGe arranged on at least one first layer of material whose refractive index is less than that of silicon, wherein a germanium concentration in the portion of SiGe varies continuously between a first value and a second value which is greater than the first value, along a direction which is approximately perpendicular to a face of the first layer on which the portion of SiGe is arranged, the first value corresponding to the germanium concentration of a face of the portion of SiGe facing the first layer, and in which a summital part of the portion of SiGe in which the germanium concentration is equal to the second value is in contact with a gas and/or a material whose refractive index is less than that of silicon.

Such a device forms a waveguide which allows more efficient non-linear conversion, for example from the MidIR domain to the NIR range, to be achieved due to the use of a portion of SiGe with a vertical refractive index gradient. For a given output power, this improvement of the conversion efficiency means that the power of the signals that have to be injected into the conversion device can be reduced.

Moreover, such device enables to have dispersion values approximately at the same level in all the MidIR domain, thus avoiding a configuration of a pump signal source over a wide band in order to maintain phase matching.

Such a portion of SiGe also allows the chromatic dispersion of the device to be reduced, in particular in TM mode, over a wider wavelength range, thus improving the conversion efficiency of the device. Thus with such a device, for a first signal to be converted with a wavelength in a given range of values, the pump signal wavelength range which resides in the zero dispersion wavelength region and therefore allows conversion of the first signal into a second signal of wavelength in a second range is narrower than that required with devices from the prior art, for example of the SOS type, in to achieve the same conversion.

The wavelength of the first infrared signal may be between about 3 μm and 7.5 μm, and the wavelength of the second infrared signal may be between about 1.3 and 1.9 μm.

The device may form a waveguide which is suitable for receiving as an input signal the first infrared signal and a pump signal whose wavelength is different from those of the first infrared signal and of the second infrared signal, for example equal to 2 μm, with the SiGe portion forming a core of the waveguide in which the non-linear conversion is able to take place.

The first layer may comprise $SiO_2$ or sapphire.

The second value of the germanium concentration in the portion of SiGe may be greater than about 20% or greater than about 30% or may be between about 30% and 40%.

The summital part of the portion of SiGe and the lateral flanks of the portion of SiGe may be in contact with air or at least one gas or $SiO_2$ or sapphire. When the device is used to make a gas sensor the summital part of the portion of SiGe and the side flanks of the portion of SiGe may preferably be in contact with the gas or gases to be analysed or with air.

The device may include in addition a second layer which is silicon-based and arranged between the first layer and the portion of SiGe. When the first layer is $SiO_2$-based and the device includes the silicon-based second layer, the first layer may correspond to a buried dielectric layer of an SOI ("Silicon-On-Insulator") substrate and the second layer may correspond to the superficial semi-conductive layer of the SOI substrate.

The thickness of the second layer may be less than or equal to about 0.3 μm.

The second layer may include a portion of silicon on which the portion of SiGe is arranged, wherein said portion of silicon may include, in a plane parallel to said face of the first layer, a width and a length which are approximately similar to a width and a length respectively of the portion of SiGe, and may include a thickness, perpendicular to said face of the first layer, which is greater than the thickness of the rest of the second layer.

Alternatively, the device may include in addition a portion of silicon arranged on the first layer and on which the portion of SiGe is arranged, with said portion of silicon including, in a plane parallel to said face of the first layer, a width and a length which are approximately similar to a width and a length respectively of the portion of SiGe.

The portion of SiGe may be of an approximate rectangular parallelepiped shape and include, in a plane parallel to said face of the first layer, a width between about 0.5 μm and 0.7 μm and a length between about 1 cm and 5 cm (assuming minimum losses of about 1 dB/cm), and a height, perpendicular to said face of the first layer, of between about 1.3 μm and 1.6 μm. A length of about 2 cm allows a conversion of about 0 dB to be achieved.

Another embodiment concerns a process for making a device for non-linear conversion of a first infrared signal into a second infrared signal whose wavelength is less than that of the first infrared signal by four wave mixing, which includes at least the making of a portion of SiGe arranged on at least one first layer of material whose refractive index is less than that of silicon and such that a concentration of germanium in the portion of SiGe varies continuously between a first value and a second value which is greater than the first value in a direction which is approximately perpendicular to one face of the first layer on which the portion of SiGe is made, and in which a summital part of the portion of SiGe in which germanium concentration is equal to the second value is in contact with a gas and/or with a material whose refractive index is less than that of silicon.

Another embodiment concerns a process for making a device suitable for a non-linear conversion of a first infrared signal into a second infrared signal whose wavelength is less than that of the first infrared signal by four wave mixing, which includes at least the making of a portion of SiGe arranged on at least one first layer of material whose refractive index is less than that of silicon and such that a concentration of germanium in the portion of SiGe varies continuously between a first value and a second value which is greater than the first value in a direction which is approximately perpendicular to a face of the first layer on which the portion of SiGe is made, the first value corresponding to the germanium concentration of a face of the portion of SiGe facing the first layer, and in which a summital part of the portion of SiGe in which the germanium concentration is equal to the second value is in contact with a gas and/or a material whose refractive index is less than that of silicon.

The process may include, in addition, prior to the making of the portion of SiGe, the making of a silicon-based second layer on the first layer, where the portion of SiGe may then be made on the second layer.

In this case the portion of SiGe may be made using the following steps:
  epitaxy of a layer of SiGe onto the second layer so that a germanium concentration in the layer of SiGe varies continuously between a first value and a second value which is greater than the first value in a direction which is approximately perpendicular to the said face of the first layer.
  photolithography and etching of the layer of SiGe, forming said portion of SiGe.

In this case, the step of etching the layer of SiGe may be carried out such that a part of the second layer is also etched, forming a portion of silicon on which the portion of SiGe is arranged such that the said portion of silicon includes, in a plane parallel to said face of the first layer, a width and a length that are approximately similar to a width and a length respectively of the portion of SiGe, and comprising a thickness, perpendicular to said face of the first layer, which is greater than the thickness of the rest of the second layer.

The process may include in addition, prior to the making of the portion of SiGe, the making of a portion of silicon on the first layer and on which the portion of SiGe is made, wherein said portion of silicon may include, in a plane parallel to said face of the first layer, a width and a length which are approximately similar respectively to a width and a length of the portion of SiGe.

Another embodiment relates to a gas detection device of the NDIR type device which includes at least one non-linear conversion device as described above, in which said conversion device is suitable for carrying out a detection of a gas.

BRIEF DESCRIPTION OF THE DRAWINGS

The present invention will be better understood by reading the description of examples of embodiments, which are given for purely informative purposes and which are in no way restrictive, whilst referring to the appended diagrams in which.

Identical, similar or equivalent parts of the various figures described hereafter bear the same numerical references so as to facilitate moving from one figure to another.

In order to make the figures more readable the various parts represented in the figures are not necessarily shown at a uniform scale.

The different possibilities (variants and embodiments) must be understood as not being exclusive of each other and may be combined together.

DETAILED DESCRIPTION OF SPECIFIC EMBODIMENTS

Figure 3:
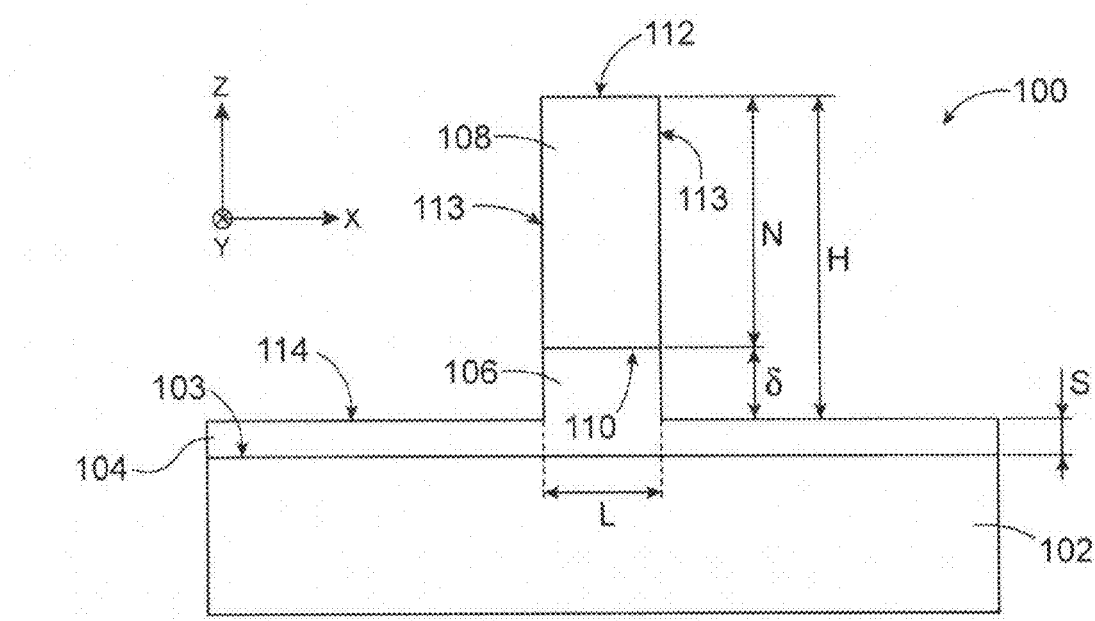
FIG. 3 is a schematic representation of a device for non-linear conversion of a first infrared signal into a second infrared signal according to a first embodiment.

Reference is made first of all to FIG. 3 which represents a four-wave mixing non-linear conversion device 100 according to a first embodiment, intended to carry out the conversion of a first infrared signal into a second infrared signal with a wavelength which is less than that of the first infrared signal. In this first embodiment, the first infrared signal has a wavelength of between about 3 µm and 7.5 µm (MidIR type signal) and the second infrared signal has a wavelength between about 1.3 µm and 1.7 µm (NIR-type signal).

The device 100 includes a first layer 102 comprising $SiO_2$, whose thickness (dimension along the Z axis shown in FIG. 3) is for example between about 1 µm and 10 µm and is here equal to about 2 µm, on which a second silicon-based layer 104 is arranged. Alternatively the first layer 102 could be sapphire-based. According to one alternative the device 100 might not comprise the first layer 102, with the lower face of the second layer 104 being in this case in contact with air. The device 100 could in addition include a support layer for example made of silicon, not shown in FIG. 3, on which the first layer 102 rests. The second layer 104 includes a portion of silicon 106 whose thickness (dimension along the Z axis shown in FIG. 3, corresponding to the dimension perpendicular to a face 103 of the first layer 102 on which the second layer 104 is arranged) is greater than a thickness S of the rest of the second layer 104. The thickness S is for example equal to about 0.2 µm, or between about 0 and 0.3 µm (a thickness of 0 corresponds to a device which does not include the second layer 104, as described later in connection with FIG. 11).

The thickness of the portion of silicon 106 which corresponds to the sum of dimensions S and δ shown in FIG. 3 is, for example, equal to about 0.7 µm or between about 0.5 µm and 1.6 µm, where δ corresponds to the difference between the thickness of the portion of silicon 106 and the thickness S of the rest of the second layer 104, and is here equal to about 0.5 µm or between 0.5 µm and 0.6 µm.

The device 100 also includes a portion of SiGe 108 arranged on the portion of silicon 106. The portion of silicon 106 includes, in a plane which is parallel to face 103 of the first layer 102, a width and a length (dimensions along the X and Y axes shown in FIG. 3, that is, the dimensions in a plane parallel to the face 103 of the first layer 102) which are approximately similar to a width L and length M (not visible in FIG. 3) respectively of the portion of SiGe 108. The portion of SiGe 108 is here of approximately rectangular parallelepiped shape and includes a width L of between 0.5 µm and 0.7 µm and which is for example equal to about 0.6 µm, and a length M between about 1 cm and 2 cm, and a thickness N (dimension perpendicular to face 103 of the first layer 102) of between about 1.1 µm and 1.6 µm and which is for example equal to about 1.3 µm. A height H may therefore be defined which corresponds to the sum of dimensions N+δ, of between about 1.7 µm and 2.1 µm and which is here equal to about 1.8 µm. When the dimension δ is close to 0, the height H may be between about 1.5 µm and 2.8 µm, without modifying phase matching constraints in the device 100.

An upper face 114 of the second layer 104 as well as the lateral walls, or side walls, of the portion of silicon 106 and of the portion of SiGe 108 and the summital part 112 of the portion of SiGe 108 are in contact with air. Alternatively, it is possible for these elements to be surrounded with a gas and/or a material which exhibits a refractive index which is less than that of silicon such as, for example, $SiO_2$ or sapphire.

The SiGe of the portion 108 has a germanium concentration which increases linearly with its thickness. Alternatively it is possible for this increase not to be linear. The germanium concentration in the portion of SiGe 108 varies continuously between a first value and a second value which is greater than the first value along a direction which is approximately perpendicular to the face 103 of the first layer 102 (direction parallel to the Z axis). The first value corresponds to the germanium concentration of the part of the portion of SiGe 108 which is in contact with the portion of silicon 106, at a face 110 of the portion 108 and has a value which is, for example, approximately zero (and therefore close in character to silicon). The second value corresponds to the germanium concentration at a summital part 112 of the portion 108 and is, for example, between about 30% and 40% or more generally greater than about 20%.

This device 100 forms a waveguide which is suitable for carrying out four-wave mixing non-linear conversion, and in particular here by degenerate four-wave mixing, of a first infrared signal of type MidIR into a second infrared signal of type NIR. The first infrared signal is intended to be introduced at an input to the device 100 which corresponds to one of the faces of the portion of SiGe 108 located in a plane which is parallel to the plane (X,Z) which can be seen in FIG. 3. A pump signal with a wavelength which is different to those of the first infrared signal and of the second infrared signal intended to be obtained at the output of the device 100 is also applied at the input to the device 100. Alternatively these signals may be injected into the device 100 after passing beforehand through a lateral coupler, for example of the evanescent coupler type.

The specific structure of the device 100 is formed by an embedded material which exhibits a low refractive index (which corresponds to the first layer 102 whose material exhibits an optical index which is less than that of silicon), silicon (which corresponds to the second layer 104 and to the portion 106) and a portion of SiGe 108 with a proportion of germanium which increases in the Z direction (perpendicular to the main faces of the layer 102) and forms a waveguide which has the effect of highly localising the field in the part of the guide where the proportion of germanium is greatest, that is at the summital part 112 of the SiGe portion 108. Such localisation promotes the non-linear interactions that are designed to occur in the device 100 in order to achieve four-wave mixing non-linear conversion, in particular degenerate four-wave mixing non-linear conversion, and to minimise the proportion of the field in the first layer 102 in order to minimise optical losses in the waveguide for the first infrared signal which it is intended to convert.

The increase in the proportion of germanium beyond 20% in the portion of SiGe 108 also has the effect of increasing optical losses in the NIR range which is here the domain of the idler signal wavelengths, or second infrared signal, intended to be obtained at the output from the device 100, since the germanium absorbs wavelengths of less than about 2.1 μm.

The design parameters for the device 100 are therefore chosen in order to achieve the best compromise between these various effects, where these parameters correspond to the materials and dimensions of the elements of the device 100 which are described above. Furthermore, the fact that the portion of SiGe 108 is arranged on the portion of silicon 106 whose thickness is greater than that of the rest of the second layer 104 allows the mode to be kept away from the material of low refractive index of the first layer 102 which generates a high level of losses in the MidIR range.

Figure 1:
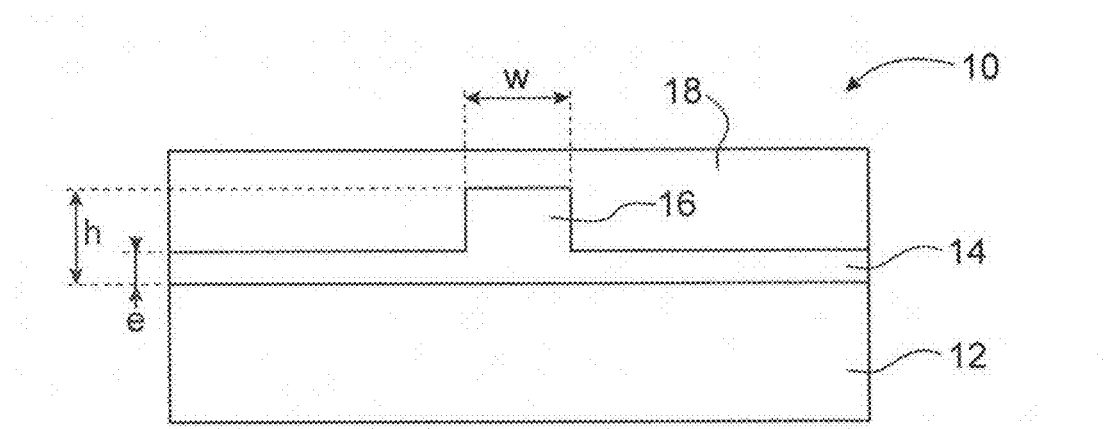
FIG. 1 is a schematic representation of a waveguide of the SOS type according to the prior art.
Figure 2:
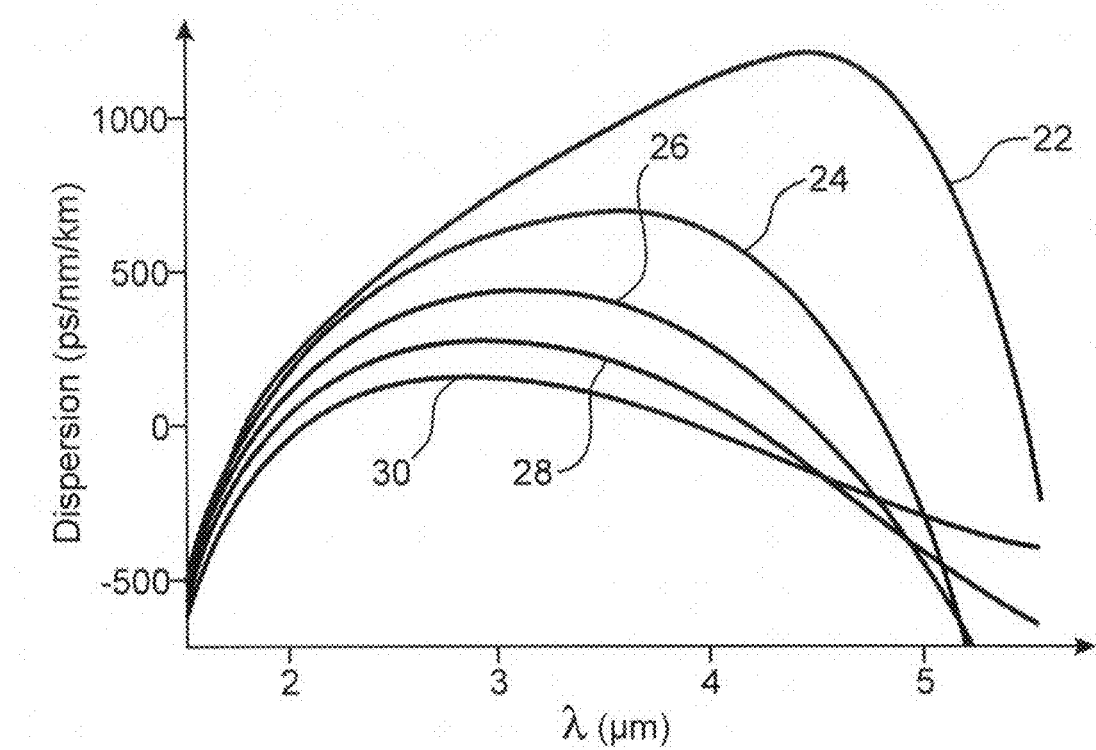
FIG. 2 shows plots of chromatic dispersion as a function of the wavelength of the waveguide represented in FIG. 1.
Figure 4:
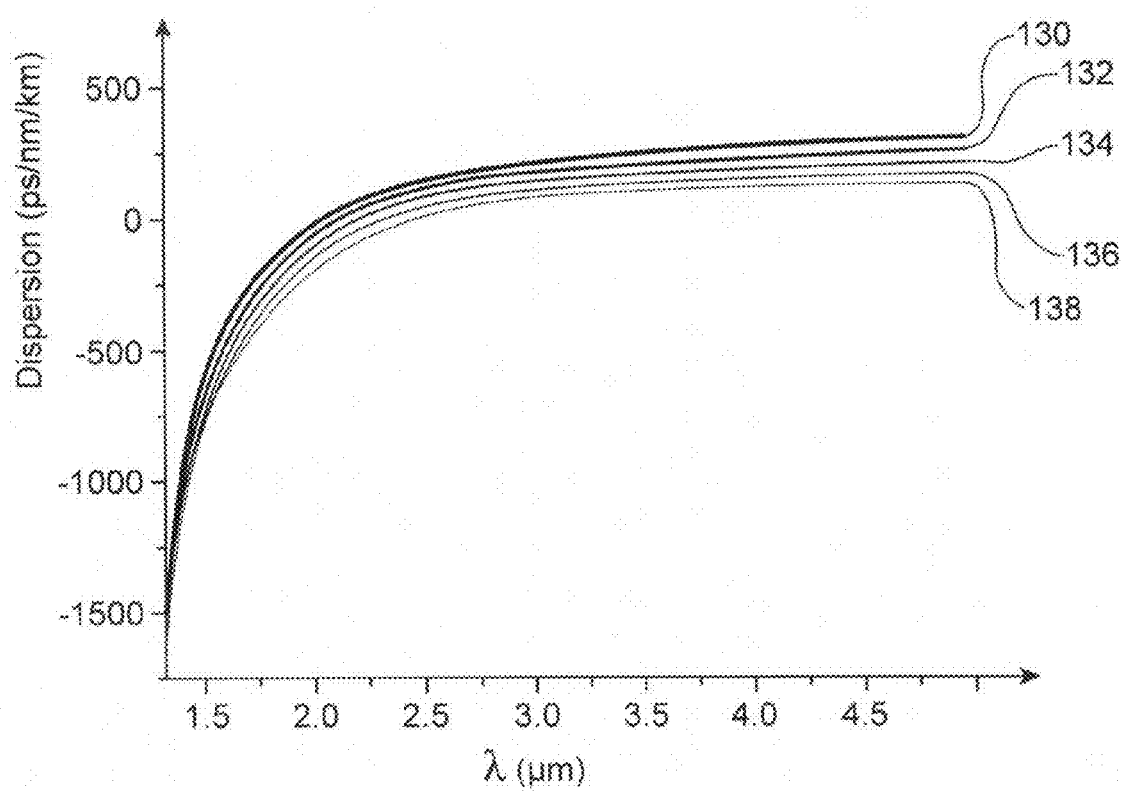
FIG. 4 shows plots of chromatic dispersion as a function of the wavelength of the non-linear conversion device according to the first embodiment.

Chromatic dispersion plots (in ps/nm/km) as a function of the wavelength (in μm) for the device 100 are shown in FIG. 4 for various values of the height H (plot 130: H=1.7 μm; plot 132: H=1.8 μm; plot 134: H=1.9 μm; plot 136: H=2 μm; plot 138: H=2.1 μm). It can be seen in this figure that the chromatic dispersion of the TM mode of the device 100 is flatter in the MidIR wavelength range than that obtained in the SOS technology as described earlier in connection with FIG. 2. In fact the design of the device 100 (dimensions, materials, level and gradient of the germanium concentration in portion 108) is adjusted in order to set the wavelength of zero dispersion (that which satisfies the relationship (2) described previously) at the selected pump signal wavelength. At this wavelength the pump signal is in phase with the signal that is to be converted, which maximises the conversion efficiency. The flatter the dispersion plot for the non-linear conversion device, and the closer it is to zero, the higher the conversion being achieved and the less the requirements of phase matching of the pump signal (or pump tunability). Thus a pump signal of wavelength close to 2.1 μm (varying by about 25 nm around this value), will be in phase with a first infrared signal to be converted which varies over a large range of values (for example between about 4.1 μm and 4.8 μm) in order to allow this conversion to take place. On the other hand in cases of SOS type waveguides from the prior art, the pump signal wavelength has to be adjusted between 2.18 μm and 2.38 μm, that is an adjustment over a band width of about 200 nm in order to meet the same conditions for phase matching and to allow conversion of an infrared signal in the band 4.2 μm-5.2 μm.

Figure 5:
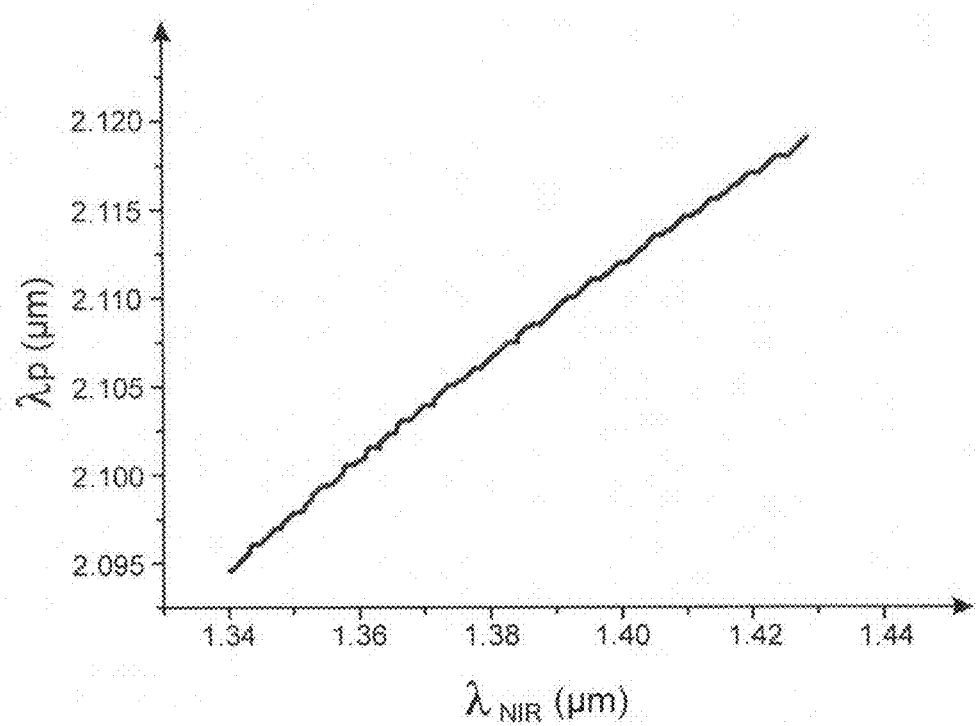
FIG. 5 shows a wavelength of a second infrared signal which may be obtained with a conversion device as a function of the wavelength of a pump signal used, for a first infrared signal of the MidIR type.

The plot shown in FIG. 5 shows the wavelength $\lambda_{NIR}$ of the second infrared signal (abscissa) that can be obtained with the device 100 as a function of the wavelength $\lambda_P$ of the pump signal (ordinate), for a first infrared signal of the MidIR type.

Another advantage of the device 100 relative to devices from the prior art, and in particular those of the SOS type, relates to the conversion efficiency achieved, which is much greater. Calculations of the conversion efficiency have been made on a device by considering the actual overlap of the modes of the pump signal, of the first infrared signal of MidIR type of wavelength equal to about 4.5 μm and of the second NIR infrared signal which varies between about 0.6 and 0.9 depending on the MidIR wavelength considered and propagation losses of about 2 dB/cm. The size of the mode in the device 100 depends on the wavelength of the first infrared signal and on the geometry of the waveguide formed by the device 100. Under these conditions, for an energy density, or pump power density, of about 0.1 GW/cm$^2$, the conversion efficiency is about −6 dB. Thus in the device 100 the power introduced in order to achieve an energy density of about 0.1 GW/cm$^2$ is only 1 W, which is much less than the 10 W required for an SOS-type waveguide. In addition, for an increase in the pump signal of about 3 dB (that is 2 W introduced in total), the conversion efficiency increases with the square of the power, that is about 6 dB for a total conversion of 0 dB.

Figure 6:
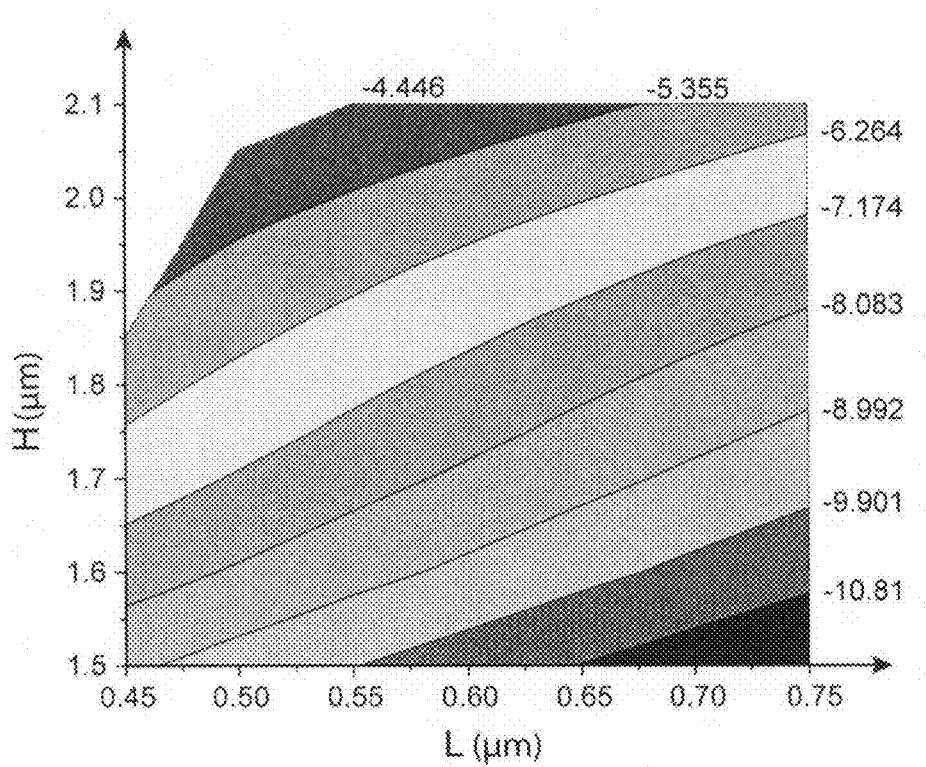
FIGS. 6 et 7 represent a variation of the conversion efficiency of a conversion device as a function of the geometric parameters of the device of lengths of 1 cm and 2 cm respectively.
Figure 7:
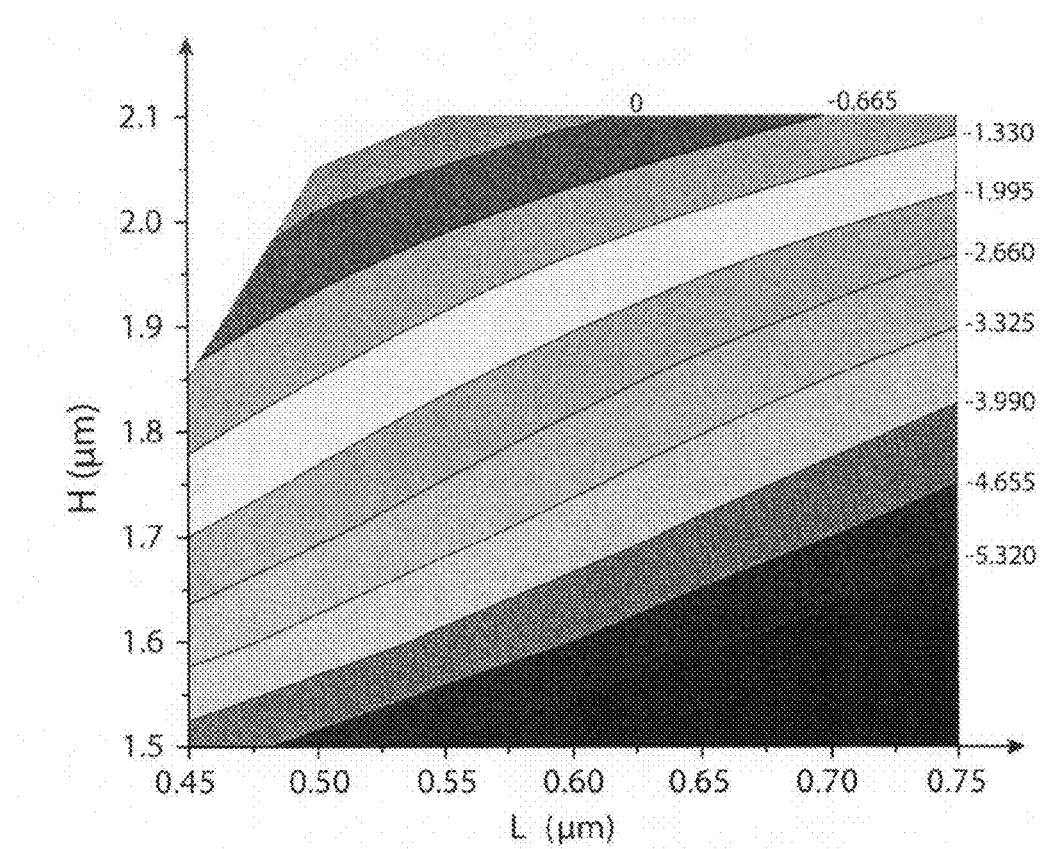

The plots in FIG. 6 show the variation in the conversion efficiency (in dB) for the device 100 as a function of the parameters H and L (in μm) for a length M=1 cm. The plots in FIG. 7 show the variation in the conversion efficiency (in dB) for the device 100 as a function of the parameters H and L (in μm) for a length M=2 cm. Since the losses in the device 100 are relatively low, it can be seen that the longer the waveguide formed by the device 100 (the greater the value of M), the more efficient is the conversion carried out by the device 100. The geometry of the waveguide, that is, the dimensions of the various elements 104, 106, and 108 of the device 100 is defined as a function of these design rules in order to maximise the conversion efficiency of the device 100.

Figure 8:
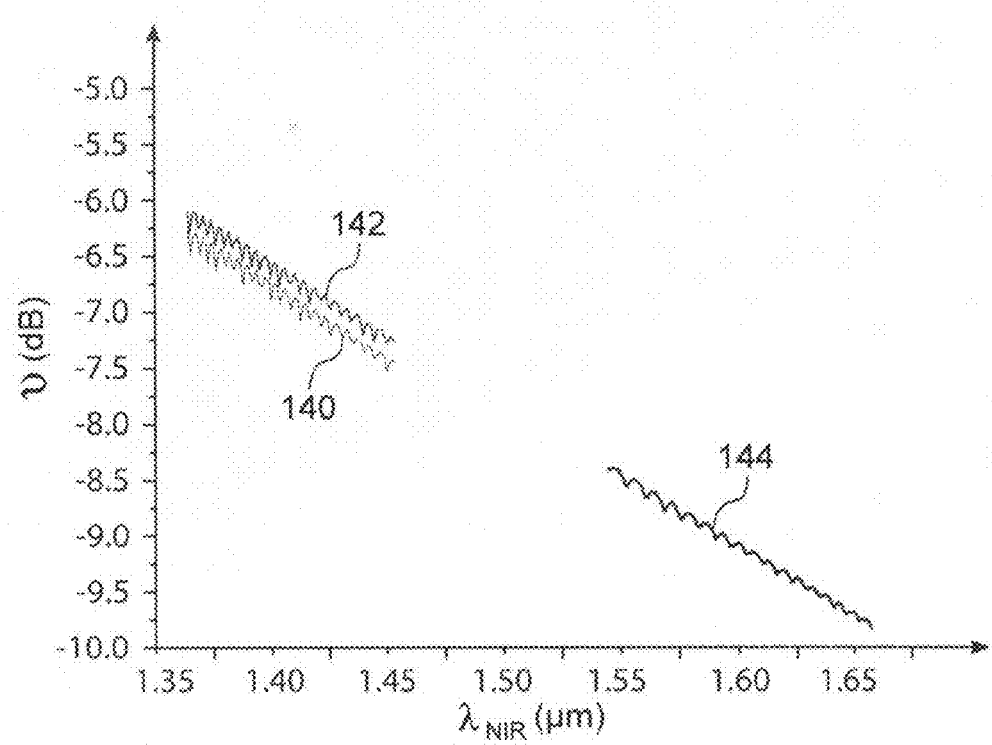
FIG. 8 shows plots representing the conversion efficiency of the conversion device as a function of the wavelength of the second infrared signal and of the gradient of variation of the germanium concentration in a portion of SiGe in the device.

The plots shown in FIG. 8 illustrate the effect that the slope of the germanium concentration gradient in the portion of SiGe 108 has (plot 140: gradient of 0.1 μm$^{-1}$; plot 142: gradient of 0.133 μm$^{-1}$; plot 144: gradient of 0.2 μm$^{-1}$; with these gradients corresponding to variations of the index per micron and which may be linear or slightly parabolic) for a given geometry of the device 100 (here H=2.05 μm, δ=1 μm, L=550 nm and M=1 cm) on the conversion efficiency v of the device, in dB, and as a function of the wavelength of the second infrared signal. It can be seen in this figure that the change in gradient has an influence not only on the conversion efficiency of the device 100 but also on the spectral range of the second infrared signal which may be obtained at the output of the device 100. Here the optimum is located at a gradient equal to 0.133 μm$^{-1}$ for a desired output wavelength (of the second infrared signal) of about 1.4 μm, and which corresponds to a maximum Ge concentration of 37% at the summital part 112 of the portion of SiGe 108.

In the first embodiment described previously, the device 100 does not include an upper cladding. Indeed, the summital part 112 and the lateral flanks 113 of the portion of SiGe 108 are not arranged against a material of low refractive index (less than that of silicon) intended to confine the transmitted fields within the portion 108, but are in contact with the air. The field of the device 100 extends significantly beyond the guiding structure, that is, beyond the portion of SiGe 108. This is also the case to a lesser extent if the summital part 112 and the lateral flanks 113 of the portion of SiGe 108 are arranged against a thin layer of material of low refractive index. The portion of SiGe 108 may therefore also function as a gas sensor. The gas molecules in the vicinity that "see" the evanescent electromagnetic field around the waveguide absorb light and generate losses which are proportional to the concentration of the gas. By creating an encapsulated reference path, that is, a portion of SiGe similar to portion 108 but which is not in contact with the gas as portion 108 is, and which only carries out conversion of wavelengths to the NIR domain, and a path which simultaneously carries out the sensor and conversion functions (portion 108 in contact with the gas), a differential measurement of the NIR signal in both branches can be used to obtain the concentration of the gas.

The structure of the device can be fully co-integrated with conventional waveguides from the microelectronics industry.

One example of a first making process of the device 100 is described in relation with FIGS. 9A-9D.

Figure 9A:
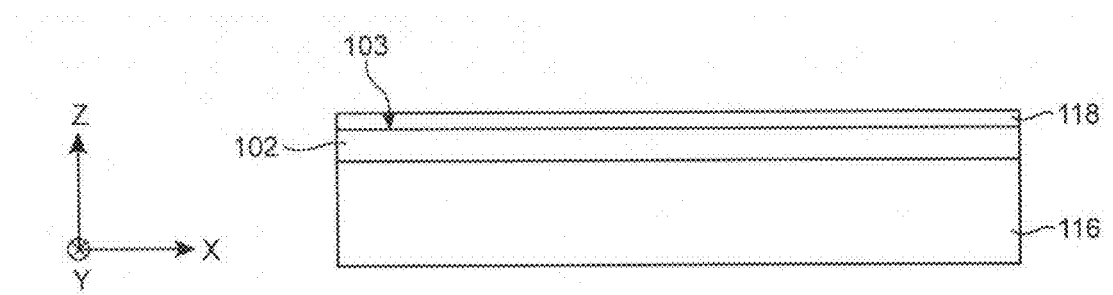
FIGS. 9A-9D represent the steps in a first example of a making process of a conversion device according to the first embodiment.

The device 100 is made from an SOI substrate which includes a silicon-based support layer 116, the first layer 102 of $SiO_2$ with a thickness (dimension along the Z axis) for example equal to about 2 μm and which forms the dielectric layer embedded in the substrate SOI, and a surface layer 118 of silicon with an initial thickness (dimension along the Z axis) equal to about 400 nm (FIG. 9A).

Figure 9B:
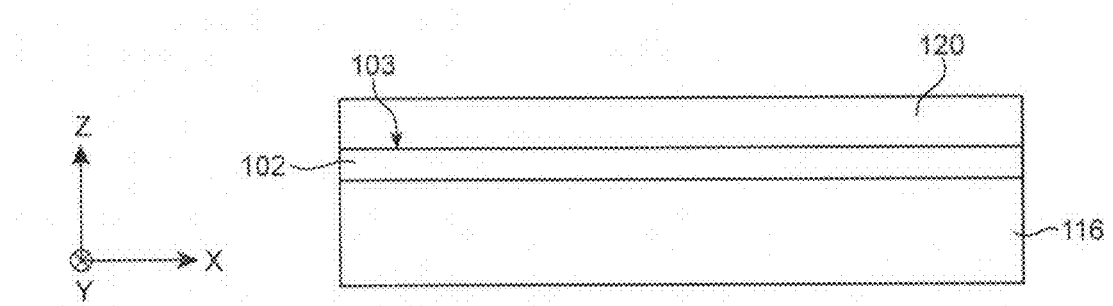

As shown in FIG. 9B, a step involving growing silicon by epitaxy is used to form an additional thickness of 0.3 μm of silicon on the surface layer 118. This additional thickness of silicon forms, with the surface layer 118, a layer of silicon 120.

Figure 9C:
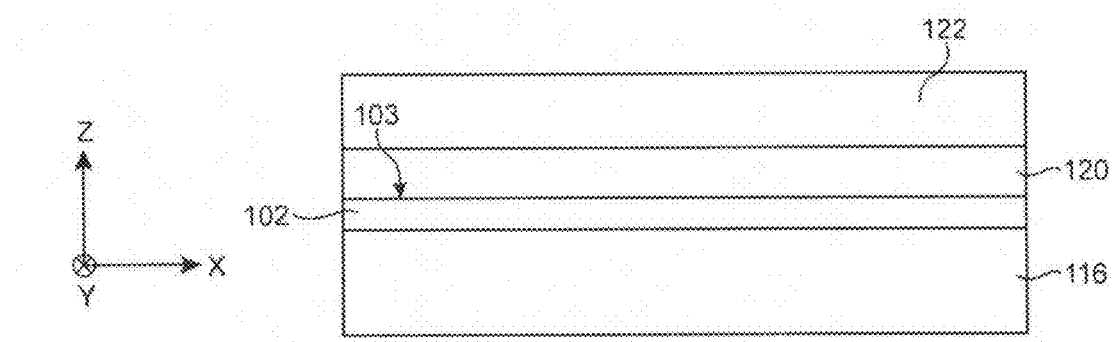

A layer of SiGe 122 is then made using epitaxy on the layer 120. This epitaxy is carried out whilst increasing the germanium concentration so that this concentration varies, for example, from 0% to about 37% along the thickness of the layer 122 (parallel to the Z axis) with a slope that is equal to about 28%/μm (FIG. 9C). The final thickness of the layer 122 is therefore equal to about 1.32 μm.

Figure 9D:
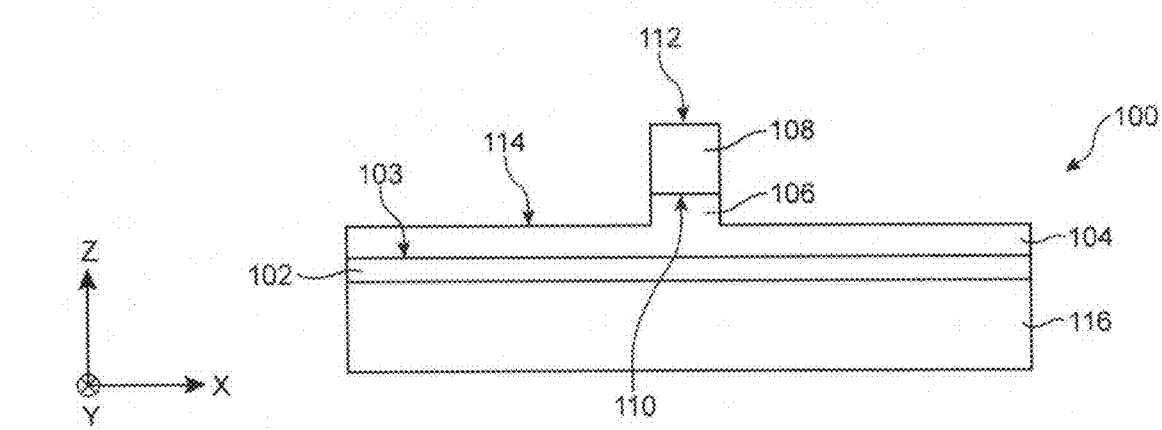

This layer 122 is then structured into the form of a waveguide using lithography then by complete etching of the thickness of the layer of SiGe 122 which is outside the lithographed zone, thus forming the portion of SiGe 108. Partial etching of the parts of the layer of silicon 120 not covered by the portion of SiGe 108 is then carried out, forming the second layer 104 with a thickness, for example, equal to about 0.2 μm as well as portion 106 with a thickness equal to about 0.5 μm (FIG. 9D).

A second example of a making process for the device 100 is described in relation with FIGS. 10A-10E.

Figure 10A:
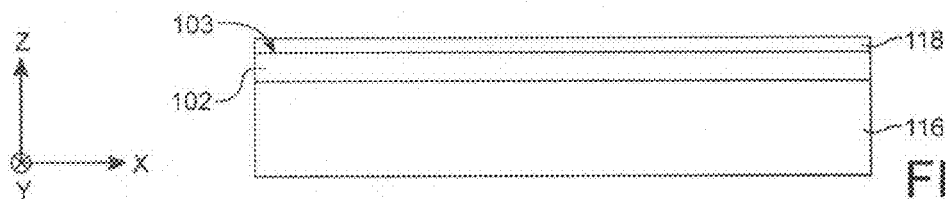
FIGS. 10A-10E represent the steps in a second example of a making process of a conversion device according to the first embodiment.

As previously described for the first example of a making process, the device 100 is made from an SOI substrate which includes the silicon-based support layer 116, the first layer 102 with a thickness, for example, equal to about 2 μm and the surface layer 118 of silicon with an initial thickness equal to about 400 nm (FIG. 10A).

Figure 10B:
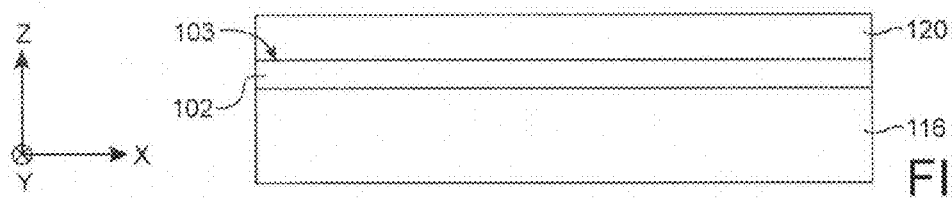

As shown in FIG. 10B, a step involving growing silicon by epitaxy is used to form an additional thickness of 0.3 μm of silicon on the surface layer 118, with this forming, with the layer 118, the silicon layer 120.

Figure 10C:
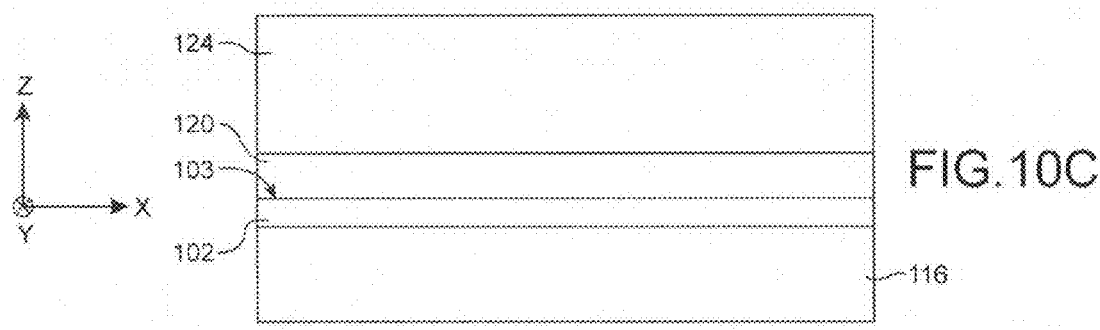

A layer of SiGe 124 is then made using epitaxy on the layer 120. This epitaxy is carried out whilst increasing the germanium concentration so that this concentration varies, for example, from 0% to about 40% over about the first half of the thickness of the layer 122 (parallel to the Z axis) with a gradient that is equal to about 28%/μm, then decreasing it again to around 0% germanium with the same gradient in the second half of the thickness of the layer 122 for a total thickness of the layer 122 equal to about 3 μm (FIG. 10C). The total germanium concentration profile in the direction perpendicular to the substrate (parallel to the Z axis) is therefore triangular.

Figure 10D:
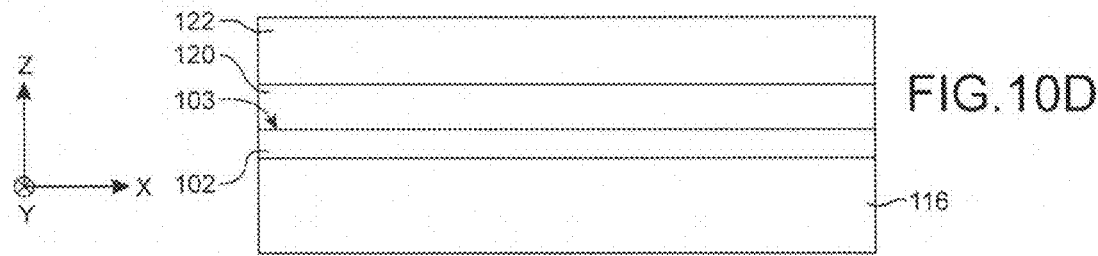
Figure 10E:
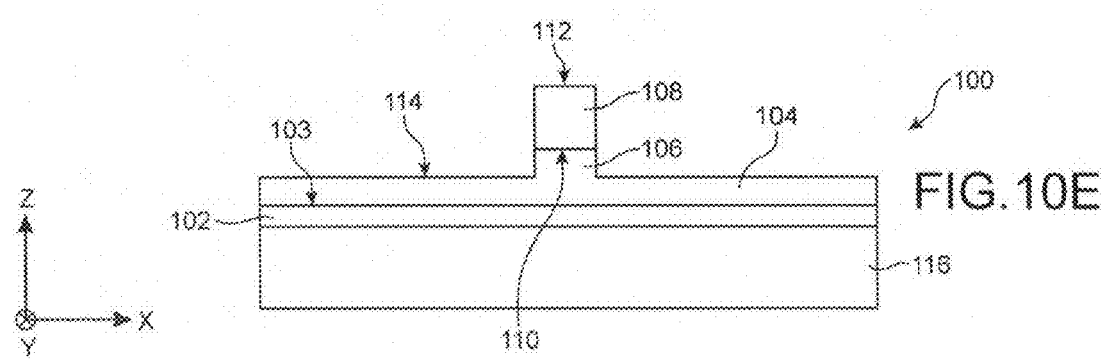

As shown in FIG. 10D, the layer 124 is then made thinner locally by etching until it reaches the Ge concentration of 37% at the part of the layer 124 which exhibits increasing germanium concentration, forming the layer 122 with a thickness equal to about 1.32 μm. The waveguide is finally structured as described previously by lithography and etching (FIG. 10E).

This second example of a making process for the device 100 has the advantage of allowing co-integration, on the same wafer, of the device 100 with optical circuitry made on the non-thinned parts of the substrate (not visible on FIGS. 10A to 10E) and which includes elements calling upon non-etched portions of the layer of SiGe 124 which exhibit a triangular-shaped concentration profile.

Figure 11:
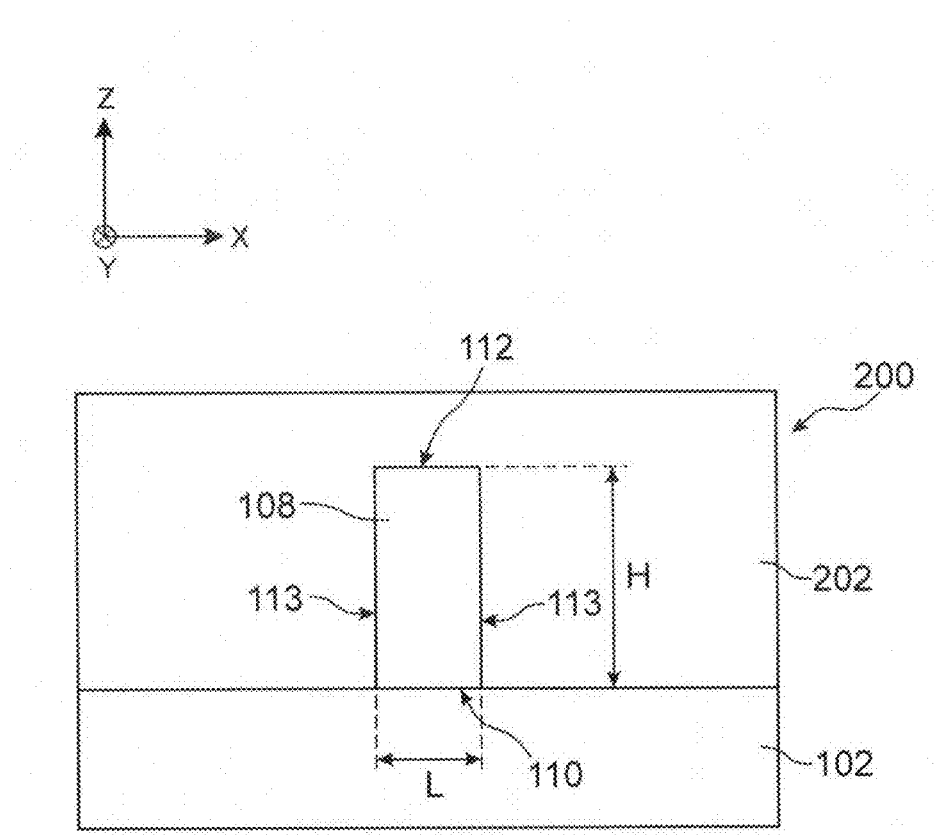
FIG. 11 is a schematic representation of a device for non-linear conversion of a first infrared signal into a second infrared signal according to a second embodiment.

With reference now to FIG. 11 which represents a four-wave mixing non-linear conversion device 200 according to a second embodiment, intended to carry out the conversion of a first infrared signal into a second infrared signal with a wavelength which is less than that of the first infrared signal. As for the first embodiment, the first infrared signal has a wavelength of between about 3 μm and 7.5 μm (MidIR type signal), and the second infrared signal has a wavelength between about 1.3 μm and 1.9 μm (NIR-type).

Like the device 100 described previously, the device 200 includes the $SiO_2$-based first layer 102 as well as the portion of SiGe 108 which exhibits a germanium concentration which increases along the direction of the thickness (parallel to the Z axis) of the portion 108. On the other hand, unlike device 100, the device 200 does not include the second silicon layer 104 formed on the first layer 102, and the silicon portion 106 arranged between the first layer 102 and the portion of SiGe 108.

Thus in the device 200, the portion of SiGe 108 is arranged directly onto the first layer 102, via, for example, PECVD-type deposition which allows the germanium composition to be varied with thickness.

In addition, the device 200 further includes a layer 202 of material of low refractive index, that is, whose refractive index is less than that of silicon, for example $SiO_2$ or sapphire. The lateral side walls of the portion of SiGe 108 as well as the summital part 112 of the portion of SiGe 108 are therefore in contact here with the material of layer 202.

Relative to device 100, this device 200 includes fewer elements to be made. On the other hand, because of the absence of the second layer 104 and of the portion 106 of silicon, this device 200 causes greater losses in the MidIR wavelength domain than the device 100. Addition of the layer 202 modifies the mode in the non-linear guide. This therefore involves adjustment of the geometric parameters of the guide.

The invention claimed is:

1. A device suitable for a non-linear conversion of a first infrared signal into a second infrared signal whose wavelength is less than that of the first infrared signal by four-wave mixing, comprising at least one portion of SiGe arranged on at least one first layer of material whose refractive index is less than that of silicon, wherein a germanium concentration in the portion of SiGe varies continuously between a first value and a second value which is greater than the first value, along a direction which is approximately perpendicular to a face of the first layer on which the portion of SiGe is arranged, the first value corresponding to the germanium concentration of a face of the portion of SiGe facing the first layer, and in which a summital part of the portion of SiGe in which the germanium concentration is equal to the second value is in contact with a gas and/or a material whose refractive index is less than that of silicon.

2. The device according to claim 1, in which the wavelength of the first infrared signal is between about 3 μm and 7.5 µm and in which the wavelength of the second infrared signal is between about 1.3 µm and 1.9 µm.

3. The device according to claim 1, where said device forms a waveguide which is suitable for receiving, as an input signal, the first infrared signal and a pump signal whose wavelength is different from those of the first infrared signal and of the second infrared signal, with the SiGe portion forming a core of the waveguide in which the non-linear conversion is able to take place.

4. The device according to claim 1, in which the first layer comprises $SiO_2$ or sapphire.

5. The device according to claim 1, in which the second value of the germanium concentration in the portion of SiGe is greater than about 20%.

6. The device according to claim 1, in which the summital part of the portion of SiGe and the lateral flanks of the portion of SiGe are in contact with air or at least one gas or $SiO_2$ or sapphire.

7. The device according to claim 1 which includes in addition a second layer which is silicon-based and arranged between the first layer and the portion of SiGe.

8. The device according to claim 7, in which the thickness of the second layer is less than or equal to about 0.3 µm.

9. The device according to claim 7, in which the second layer includes a portion of silicon on which the portion of SiGe is arranged, wherein said portion of silicon includes, in a plane parallel to said face of the first layer, a width and a length which are approximately similar to a width and a length respectively of the portion of SiGe, and which includes a thickness, perpendicular to said face of the first layer which is greater than the thickness of the rest of the second layer.

10. The device according to claim 1, which includes in addition a portion of silicon arranged on the first layer and on which the portion of SiGe is arranged, with said portion of silicon including, in a plane parallel to said face of the first layer, a width and a length which are approximately similar to a width and a length respectively of the portion of SiGe.

11. The device according to claim 1, in which the portion of SiGe is of an approximately rectangular parallelepiped shape and includes, in a plane parallel to said face of the first layer, a width of between about 0.5 µm and 0.7 µm and a length between about 1 cm and 5 cm, and a height, perpendicular to said face of the first layer which is between about 1.3 µm and 1.6 µm.

12. A NDIR-type gas detection device which includes at least one non-linear conversion device according to claim 1, in which said conversion device is suitable for carrying out a detection of a gas.

13. A process for making a device suitable for a non-linear conversion of a first infrared signal into a second infrared signal whose wavelength is less than that of the first infrared signal by four wave mixing, which includes at least the making of a portion of SiGe arranged on at least one first layer of material whose refractive index is less than that of silicon and such that a concentration of germanium in the portion of SiGe varies continuously between a first value and a second value which is greater than the first value in a direction which is approximately perpendicular to a face of the first layer on which the portion of SiGe is made, the first value corresponding to the germanium concentration of a face of the portion of SiGe facing the first layer, and in which a summital part of the portion of SiGe in which the germanium concentration is equal to the second value is in contact with a gas and/or a material whose refractive index is less than that of silicon.

14. The process according to claim 13, which includes, in addition, prior to the making of the portion of SiGe, the making of a silicon-based second layer on the first layer, where the portion of SiGe is then made on the second layer.

15. The process according to claim 14, in which the portion of SiGe is made using the following steps:
   epitaxy of a layer of SiGe onto the second layer so that a germanium concentration in the layer of SiGe varies continuously between a first value and a second value which is greater than the first value in a direction which is approximately perpendicular to the said face of the first layer.
   photolithography and etching of the layer of SiGe, forming the said portion of SiGe.

16. The process according to claim 15, in which the step of etching the layer of SiGe is carried out such that a part of the second layer is also etched, forming a portion of silicon on which the portion of SiGe is arranged such that the said portion of silicon includes, in a plane parallel to said face of the first layer, a width and a length that are approximately similar to a width and a length respectively of the portion of SiGe, and comprising a thickness, perpendicular to said face of the first layer, which is greater than the thickness of the rest of the second layer.

17. The process according claim 13, which includes in addition, prior to the making of the portion of SiGe, the making of a portion of silicon on the first layer and on which the portion of SiGe is made, wherein said portion of silicon includes, in a plane parallel to said face of the first layer, a width and a length which are approximately similar to a width and a length respectively of the portion of SiGe.

* * * * *